United States Patent [19]

Fischell

[11] Patent Number: 4,671,261

[45] Date of Patent: Jun. 9, 1987

[54] PENILE ERECTION DEVICE WITH VALVING IN THE PENILE CYLINDER

[76] Inventor: Robert E. Fischell, 1027 McCeney Ave., Silver Spring, Md. 20901

[21] Appl. No.: 822,211

[22] Filed: Jan. 24, 1986

[51] Int. Cl.⁴ .............................................. A61F 2/26
[52] U.S. Cl. ..................................................... 128/79
[58] Field of Search ......................................... 128/79

[56] References Cited

U.S. PATENT DOCUMENTS

| | | |
|---|---|---|
| 4,224,934 | 9/1980 | Scott et al. ............................ 128/79 |
| 4,378,792 | 4/1983 | Finney ................................... 128/79 |
| 4,550,720 | 11/1985 | Trick ..................................... 128/79 |
| 4,559,931 | 12/1985 | Fischell ................................. 128/79 |
| 4,572,168 | 2/1986 | Fischell ................................. 128/79 |

FOREIGN PATENT DOCUMENTS 0000302  3/1980  PCT Int'l Appl. ................... 128/79

Primary Examiner—Robert Peshock
Assistant Examiner—Cary E. Stone
Attorney, Agent, or Firm—Fleit, Jacobson, Cohn & Price

[57] ABSTRACT

The penile erection device with valving in penis of the present invention includes a simple, safe, reliable, easy to operate and inconspicious implantable device wherein the impotent male achieves a penile erection that is physiological normal. The erect state is achieved rapidly by pushing the penis upward against the abdomen thereby opening a valve located within a stiffener cylinder inside the corpus cavernosum without requiring pumping or manual squeezing of the reservoir containing the fluid that is to be displaced into the pendulous portion of the penile stiffener cylinder. The flaccid penile state is achieved rapidly by pushing the penis upward against the abdomen thereby opening the valve while simultaneously squeezing the penis.

36 Claims, 4 Drawing Figures 4,671,261

PENILE ERECTION DEVICE WITH VALVING IN THE PENILE CYLINDER

BACKGROUND OF THE INVENTION

1. Field of the Invention

This invention relates to an improved, manually actuated, hydraulic device to provide a penile erection for human males who suffer the dysfunction of erectile impotence.

2. Description of the Prior Art

The normal male achieves an erection when a multitude of small blood vessels within a long cylindrical section on each side of the penis, called the corpus cavernosum, fill with blood as a result of an increase in the vessels' output resistance to blood flow. There are two such parallel cylinders in the penis (the plural being the corpora cavernosa) which simultaneously become engorged with blood, thereby producing a penile erection. Unfortunately, there are in the United States alone, 10 million men who are unable to achieve a penile erection.

There are many causes for impotency in the human male, both psychological and physiological. Among the physiological causes are: long term diabetes, damage to the spinal cord, multiple sclerosis, a surgical procedure in the lower abdomen that has caused nerve damage in the genital region, and advanced age. Such impotence often destroys the male's psychological well being, and often seriously disrupts or even causes the dissolution of an otherwise fulfilling relationship. It is therefore not surprising to find that the patent art is replete with examples of artificial penile erection devices.

U.S. Pat. No. 4,559,931, issued to Fischell on Dec. 24, 1985, describes a penile erection device that is improved by eliminating a pump in the scrotum and by effecting the desired pumping action with a single thrust. This invention still requires two parts of the system to be implanted outside of the penis itself. The disadvantage of this design is that it requires more extensive surgery as compared with implanting only one part of the system outside of the corpus cavernosum.

A patent application by Fischell, Ser. No. 526,893, now U.S. Pat. No. 4,596,242 filed Aug. 26, 1983, describes two parts of a penile erection device that are located outside of the penis itself. This device utilizes a vapor-pressure actuated mechanism that eliminates manual pumping to effect the erectile state. This invention also requires two parts of the system to be implanted outside the corpus cavernosum of the penis.

Another application by Fischell, Ser. No. 563,455, filed Dec. 20, 1983, now U.S. Pat. No. 4,572,168, describes a vapor-pressure actuated penile erection device and method in which the fluid reservoir is vapor-pressure actuated. The fluid reservoir has a significant volume limitation in that the entire reservoir must be contained within the root of the corpus cavernosum. Furthermore, there must be two separate reservoirs, one in each of the two corpora cavernosa of the penis. The small size of the root of the corpus cavernosum definitely limits the reservoir fluid volume that can be driven into the pendulous portion of the penile cylinder which, therefore, significantly limits the increase in girth of the penis that is obtainable for the erect state.

SUMMARY OF THE INVENTION

It is, therefore, highly desirable to provide a simple, safe, reliable, easy to operate and comparatively inconspicuous implantable device whereby the impotent male can achieve a penile erection that is physiologically normal; i.e., the device should cause the penis to become longer, thicker, harder and stiffer, and to assume a generally upward angle. It is further desirable to have the penis return to a normal, flaccid condition at all other times than during sexual activity. Ideally, these two physiologically normal operating characteristics should be achievable promptly on command of an individual in whom the device is implanted.

To this end, one object of the present invention is to provide a means for readily causing the penis to achieve an erectile state which is physiologically equivalent to that of the normal male. Specifically, an object is to provide a device whereby the penis becomes longer, thicker, harder, stiffer, and attains a proper upward angle.

Another object of the present invention is to provide a penile erection device having a readily achievable and physiologically normal flaccid state.

Yet a further object of the present invention is to provide a penile erection device wherein the erectile state can be achieved rapidly by pushing the penis upward against the abdomen thereby opening a valve located within a cylinder inside the corpus cavernosum without requiring pumping or manual squeezing of a reservoir containing the fluid that is to be displaced into the pendulous portion of the penile stiffener cylinder.

Another object of the present invention is to provide a rigid reservoir within the patient's abdomen containing a comparatively large volume of fluid that is displaced into the pendulous portion of the stiffener cylinder to achieve the erectile state.

Still another object of the present invention is to provide a device wherein the flaccid penile state can be achieved rapidly by pushing the penis upward against the abdomen thereby opening a valve located within the corpus cavernosum at the base of the penis while simultaneously squeezing the penis with the same hand that holds the penis at a sharp upward angle.

A further object of the present invention is to provide an effective, fully implantable device wherein only the fluid reservoir is located outside of the corpora cavernosa.

Another object of the present invention is to provide a device wherein the reservoir is designed with a limited pressure capability so that neither of the two stiffener cylinders located in the corpora cavernosa can be over pressurized.

These and other objects of the present invention, as well as many of the attendant advantages thereof, will become more readily apparent when reference is made to the following description taken in conjunction with the accompanying drawings.

DETAILED DESCRIPTION OF THE DRAWINGS

Figure 1:
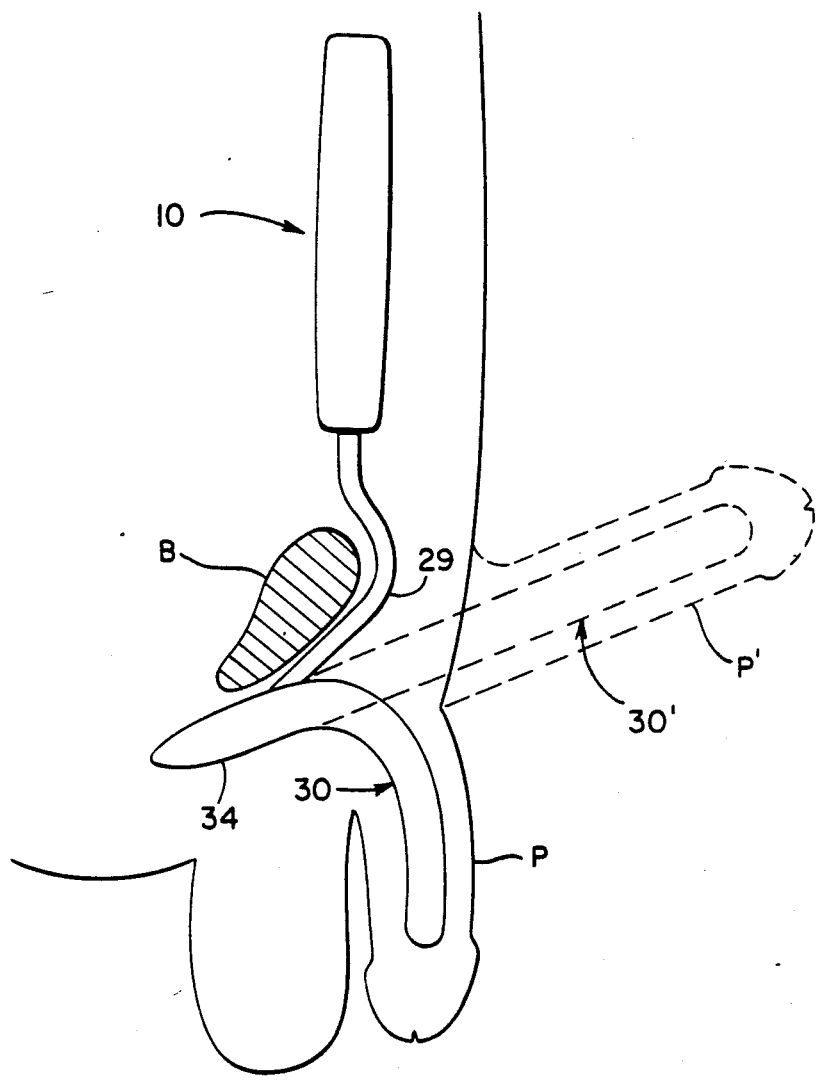
FIG. 1 shows the configuration of the present invention as it is implanted within the body showing the penis in both the flaccid and erect states.

FIG. 1 shows the configuration of this improved, vapor-pressure actuated penile erection device as it is implanted in a man who suffers the affliction of erectile impotence.

A reservoir 10 is connected by tubing 29 that passes, just anterior to the pubic bone B, into the inlet of an inflatable stiffener cylinder which is shown in its flaccid position at 30 and its erect position at 30' corresponding to the penis P being in its flaccid state and in the erect state at P'. The cylinder 30 includes a root section 34 that is implanted in the root of the corpus cavernosum of the penis. Although only one piece of tubing 29 and only one cylinder are shown, two pieces of connecting tubing 29 and two cylinders 30 would normally be used. In an alternate embodiment, the reservoir is located in a rear section of the inflatable stiffener cylinder to form a one-piece device.

Figure 2:
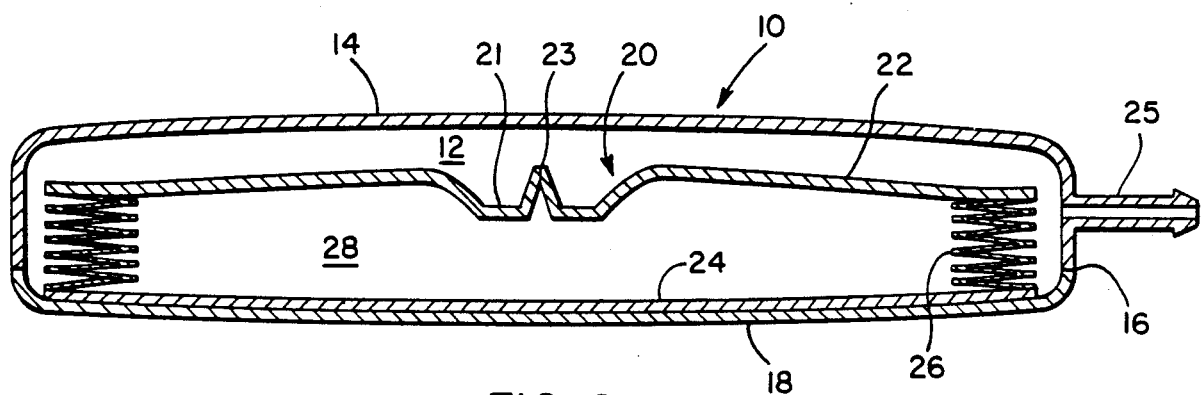
FIG. 2 is a cross sectional view of the vapor-pressure actuated reservoir.

FIG. 2 shows the configuration of a vapor-pressure actuated reservoir 10 that contains a sufficiently large fluid reservoir 12 to fill two inflatable stiffener cylinders 30. The outer shell of the reservoir consists of an upper shell 14 that is connected by a weld 16 to a bottom shell 18. Contained within the reservoir 10 is a metal bellows 20 consisting of a top cap 22 which is joined to the bottom plate 24 by bellows convolutions 26 which act together to enclose a vapor pressurant chamber 28. The top cap 22 has at its center an indentation 21 which, in turn, has at its center a fill port 23 that is welded closed after the pressurant chamber 28 is filled with the pressurant fluid.

As previously described in the above referenced application Ser. No. 526,893, the pressurant can be any one of several fluids that have a vapor pressure between 1.0 and 15 psig at body temperature. A flourocarbon having a vapor pressure between 5 and 8.3 psig at body temperature is ideally suited for this application. The ideal working fluid contained within the reservoir chamber 12 is sterile, normal saline; i.e., 0.9% NaCl in water.

Connected to the outer shell is an outlet port 25 that is joined to the connecting tubing 29 of FIG. 1. All structural materials of the reservoir are typically fabricated from pure titanium or one of its alloys. The thickness of the reservoir shells 14 and 18 is typically between 5 and 125 mils; the thickness of the bellows cap 22 and bottom plate 24 is typically 5 to 100 mils. The bellows convolutions 26 typically consist of 5 to 10 separate convolution elements each of which are 1 to 20 mils in thickness.

Figure 3:
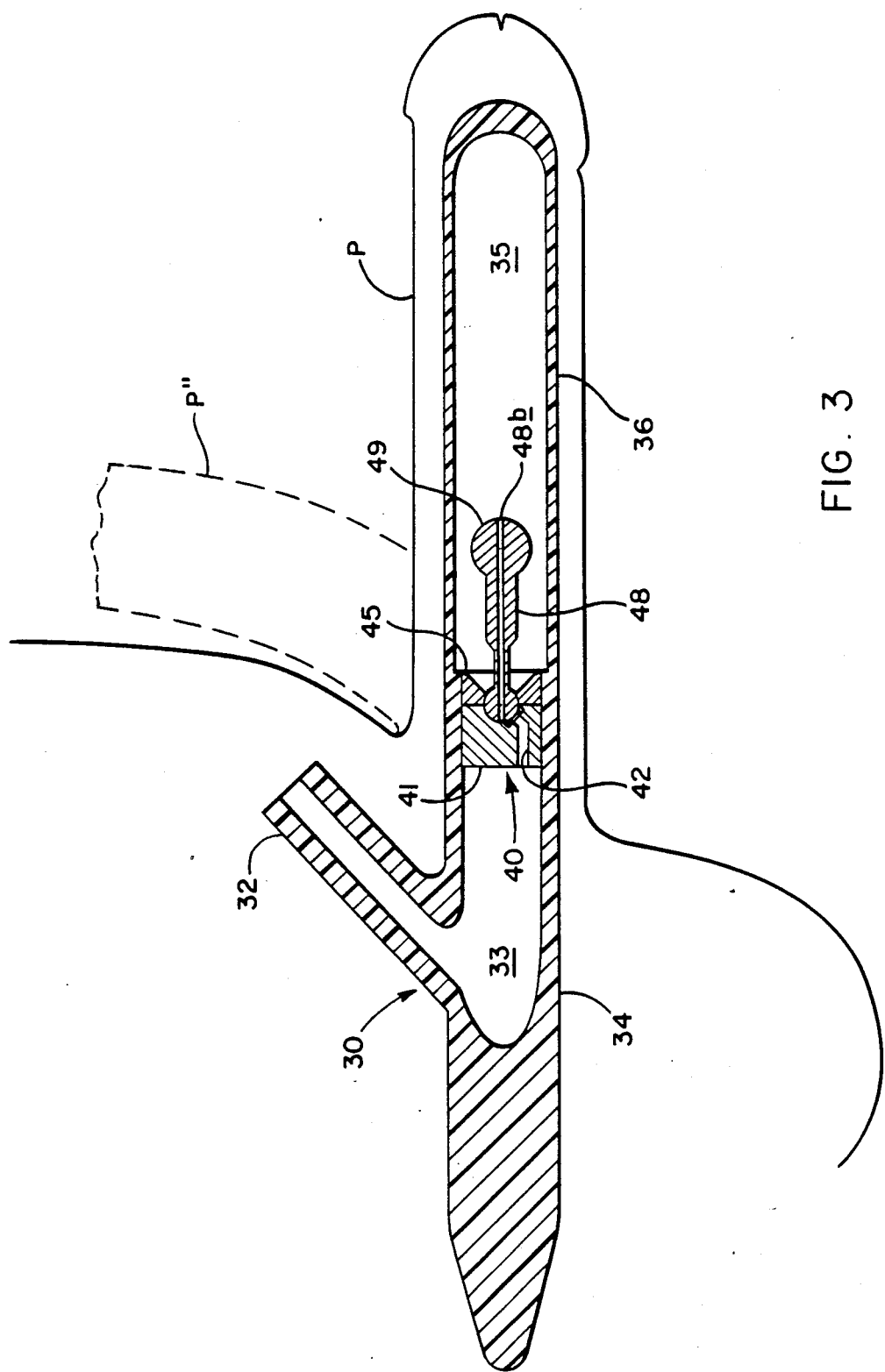
FIG. 3 is a cross-sectional view of the inflatable stiffener cylinder showing its internal valve.

FIG. 3 is a cross-sectional view of the inflatable stiffener cylinder 30 having an inlet 32 that is joined to the tubing 29 of FIG. 1. The inflatable stiffener cylinder 30 has a thickened root portion 34 and a pendulous portion 36. Contained within the inflatable stiffener cylinder 30 is a ball valve 40 having a valve base 41, a lever guide 45 and a lever 48 having a spherical end section 49. The saline solution working fluid within the root chamber 33 is normally prevented from flowing to or from the pendulous chamber 35 because the valve 40 is normally closed.

When the erect state is desired, the penis P is pushed laterally against the body until it is in the position shown by the dotted lines P'' of FIG. 3. This causes the lever passageway 48b to be in fluid communication with the valve base passageway 42 and thus allows the pressurized fluid from the reservoir 10 (of FIGS. 1 and 2) to be driven (as is described in above referenced application Ser. No. 526,893) from the root chamber 33 to the pendulous chamber 35. This pressurizes the pendulous portion 36 of the cylinder 30 to a pressure of approximately 6 psig which provides the desired erect state. When the penis is returned to the position P shown in FIG. 3, the valve 40 is closed, and even a very high pressure exerted on the pendulous portion 36 will not result in a return of fluid to the reservoir 10.

When it is desired to return to the flaccid state, the penis is once again moved laterally upward to the position P'' of FIG. 3, where the passageways 42 and 48b are aligned once more, and the penis is then squeezed which returns the fluid to the reservoir. While still holding the penis firmly, the penis is then moved downward, and when released, the flaccid state will be maintained.

Figure 4:
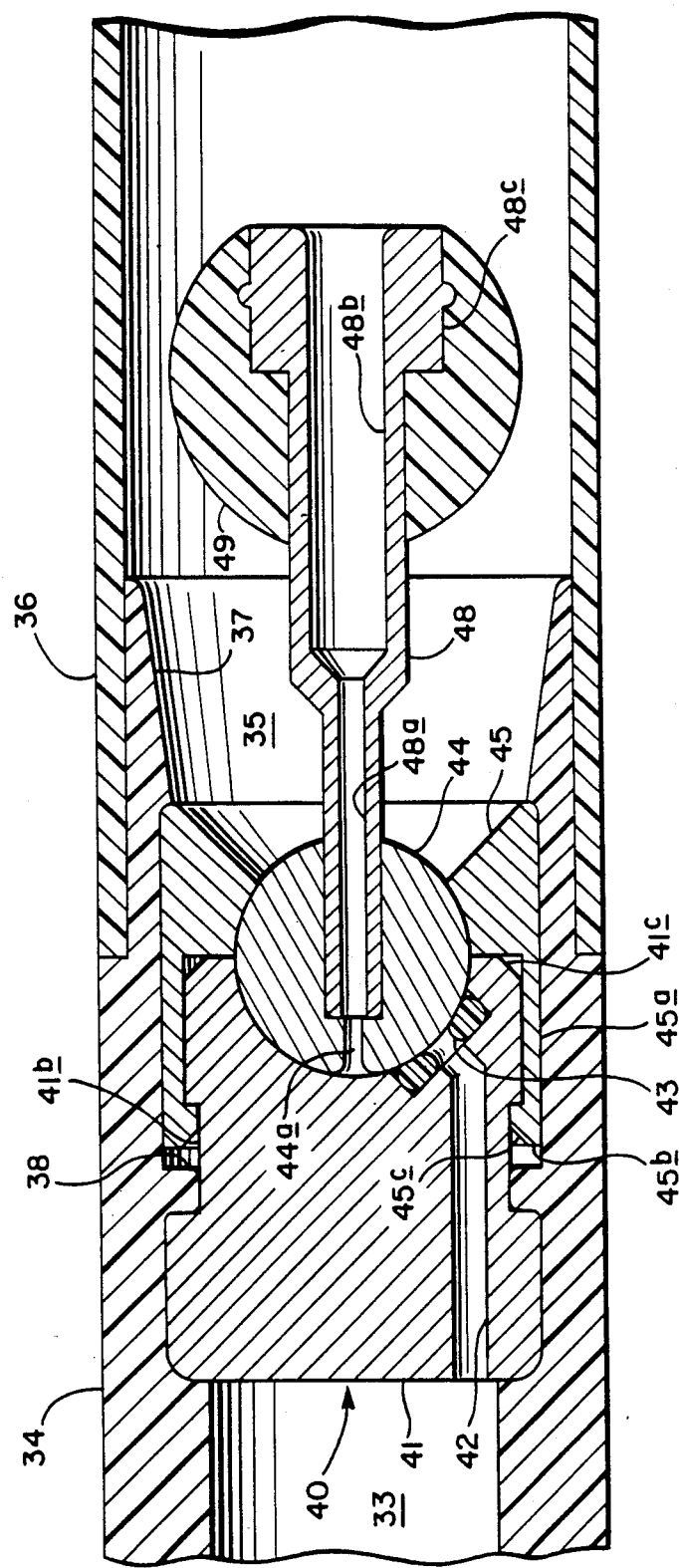
FIG. 4 is a detailed cross-sectional view of the valve that is contained within the stiffener cylinder.

A more detailed drawing of the ball valve 40 is shown in FIG. 4. A thickened silicone rubber root portion 34 is shrunk-fit onto the outside cylindrical surface of the valve base 41 and the lever guide 45. The silicone rubber pendulous portion 36 is then joined with silicone adhesive to the root portion 34. A strain relief 37 which is part of the root 34 is used to provide improved joining to the pendulous portion 36 thus allowing the assembly to better withstand frequent bending of the penis. The root 34 also has molded into it a half "O"-ring 38 that lies within the groove 41b of the base 41 which construction provides a seal that prevents fluid from passing from the root chamber 33 to the pendulous chamber 35 along the outside of the cylinders. Furthermore, this construction prevents the valve 40 from sliding axially within the cylinder root 34.

The valve base 41 is joined to the lever guide 45 by pushing the split cylinder 45a over the outside of the base 41 until its outer ridge 45b lies within the base groove 41b. The split cylinder 45a is cut through at 2 to 4 places (not shown) in a direction parallel to the axis of the root portion 34 so that the split cylinder 45a can slide easily over the outer cylindrical surface of the base 41 without excessive stress. The ease of snapping the guide 45 onto the base 41 is enhanced by the angled surface 41c of the base 41 and the angled surface 45c of the lever guide 45. This assembly takes place after the lever 48 is press fit into the ball 44 and the ball 44 is placed within the spherical cavities of the base 41 and the guide 45. Prior to this assembly, an elastomer "O"-ring 43 is placed in the "O"-ring groove within the base 41.

When the penis is moved upward against the body as previously described and as shown at P'' in FIG. 3, the lever spherical section 49 of the lever 48 is forced upward within the pendulous portion 36 which causes alignment of the base passageway 42 with the ball passageway 44a and the lever passageways 48a and 48b.

To facilitate communication between base passageway 42 and ball passageway 44a, it is contemplated that one or the other of base passageway 42 and ball passageway 44a could include a horizontally extending elongated opening. For example, a horizontally extending opening could be defined at the end of base passageway 42 so that base passageway 42 would be aligned with ball passageway 44a when the penis is in position P'' shown in FIG. 3. With this configuration, alignment occurs even though the penis is not moved precisely vertically or held in precisely a vertical position.

When alignment of base passageway 42 and ball passageway 44a occurs, fluid from the pressurized reservoir 10 (FIGS. 1 and 2) flows from the root chamber 33 successively through the base passageway 42, the interior of the "O"-ring 43, the ball passageway 44a, the narrow lever passageway 48a, the wide lever passageway 48b and finally into the pendulous chamber 35. This then provides the desired erect state. The method for obtaining the flaccid state has already been described.

The outer portions of the inflatable cylinder 30, (i.e., the root portion 34 and the pendulous portion 36) are typically made from an elastomer such as silicone rubber or polyurethane. The valve base 41 and lever guide 45 could be molded from a hard plastic material such as acetal or could be machined in titanium. The ball 44 might be made from a titanium alloy or from sapphire. In any case, its outer surface would be polished to a fine finish so that it would not abrade the "O"-ring, thus providing a long cycle life for the valve. The lever spherical section 49 might typically be fabricated from Teflon. The spherical section 49 is typically press fit onto the end section 48c before the lever guide 48 is joined to the ball 44.

Various other modifications, adaptations, and alternative designs are, of course, possible in light of the above teachings. Therefore, it should be understood at this time that within the scope of the appended claims, the invention may be practiced otherwise than as specifically described herein.

I claim:

1. A penile erection device that is fully implantable in a patient, said device comprising:
   stiffener means adapted for implantation in the penis;
   reservoir means in fluid communication with said stiffener means; and
   valve means for controlling flow between said reservoir means and said stiffener means, said valve means being movable between a first position assumed when said stiffener means is in a first position, and a second position assumed when said stiffener means is in a second position, said valve means being closed in its first position to maintain the penis in one of an erect state and a flaccid state and being open in its second position to allow the penis to change to one of the flaccid state and the erect state, and said valve means being adapted to be located in the corpus cavernosum of the penis so as to be movable to the open second position in response to manual movement of the penis laterally out of one of a flaccid state position and an erect state position of the penis, and movable to the closed first position upon movement of the penis to one of the erect state and the flaccid state positions.

2. The device of claim 1, wherein said reservoir means includes a fluid reservoir and a vapor pressurant chamber, and wherein said vapor pressurant chamber impinges on said fluid reservoir to force a working fluid from said fluid reservoir to said valve means.

3. The device of claim 2, wherein the penis changes from the flaccid state to the erect state when said valve means is opened and said working fluid is forced from said reservoir means into said stiffener means.

4. The device of claim 2, wherein the penis changes from the erect state to the flaccid state when said valve means is opened and pressure is applied to the penis to counteract the pressure of said working fluid in the stiffener means and to force said working fluid back into said fluid reservoir.

5. The device of claim 2, wherein said vapor pressurant chamber includes a fluid which expands at body temperature.

6. The device of claim 2, wherein said reservoir means includes an outlet through which said working fluid exits via a connecting means connected to said valve means to pressurize said stiffener means when said valve means is opened.

7. The device of claim 1, wherein said stiffener means includes a rigid root section outer casing for implantation in the root of the corpus cavernosum, and a flexible, distensible pendulous section outer casing for implantation in the pendulous portion of the penis.

8. The device of claim 7, wherein said reservoir means includes a sealed, variable volume pressurant chamber, a fluid reservoir chamber whose volume is dependent upon the volume of said variable volume pressurant chamber, a pressurant filling said pressurant chamber and a working fluid filling said fluid reservoir chamber, said pressurant being capable of changing state at normal body temperature in dependence upon the volume of said pressurant chamber to force working fluid from said fluid reservoir chamber.

9. The device of claim 8, wherein a pendulous chamber is located in said pendulous section outer casing, said pendulous chamber being in flow communication with said fluid reservoir chamber via said valve means, said valve means allowing the penis to change from the flaccid state to the erect state when the volume of said pressurant chamber is increased to deliver said working fluid from said fluid reservoir chamber to said pendulous chamber.

10. The device of claim 9, wherein said valve means includes a manually operated valve intermediate said fluid reservoir chamber and said pendulous chamber so that when said valve is opened, the pressurant in said pressurant chamber is permitted to expand and thereby increase the volume of said pressurant chamber.

11. The device of claim 1, wherein said valve means is movable to the open and closed positions in response to manual lateral movement of the penis upward against the patient's abdomen.

12. The device of claim 1, wherein said valve means comprises lever means for moving said valve means between the closed first position and open second position, said lever means extending into a pendulous portion of said stiffener means for movement in response to said manual lateral movement of the penis.

13. The device of claim 12, wherein said valve means comprises a fixed base member and a movable ball member, and said lever means is mounted at one end on said ball member.

14. The device of claim 13 wherein:
   said lever means comprises spherical means on an opposite free end of said lever means;
   said ball member is retained on said fixed member by one end of a guide member of split construction at an opposite end to facilitate mounting of said guide member on said base member; and
   said ball member and said lever means include respective fluid passageways in communication with one another, with the fluid passageway in said lever means opening into a fluid chamber in said pendulous portion of said stiffener means.

15. The device of claim 12 wherein said lever means comprises spherical means on a free end of said lever means.

16. The device of claim 12 wherein said ball member is retained on said fixed member by one of a guide member of split construction at an opposite end to facilitate mounting of said guide member on said base member.

17. The device of claim 12, wherein said ball member and said lever means include respective fluid passageways in communication with one another, with the fluid passageway in said lever means opening into a fluid chamber in said pendulous portion of said stiffener means.

18. A penile erection device that is fully implantable in a patient, said device comprising:
   stiffener means adapted for implantation in the penis, said stiffener means including a root portion, a pendulous portion, and a valve,
   said valve being open and allowing fluid to pass into said pendulous portion when the pendulous portion is in a predetermined position with respect to said root portion;
   a fluid reservoir being in flow communication with said pendulous portion when said valve is open; and
   a working fluid located in said fluid reservoir to flow from said fluid reservoir into said pendulous portion when said valve is open, said fluid reservoir including a working fluid chamber and a vapor pressurant chamber, and said vapor pressurant chamber impinging on said working fluid chamber to force said working fluid from said working fluid chamber to said valve.

19. The device in claim 11, wherein the penis changes from the flaccid state to the erect state when said valve is opened and said working fluid is forced from said working fluid chamber into said pendulous portion.

20. The device of claim 19, wherein the penis changes from the erect state to the flaccid state when said valve is opened and pressure is applied to the penis to counteract the pressure of the fluid in the stiffener means and to force the fluid back into said fluid reservoir.

21. The device of claim 18, wherein said vapor pressurant chamber includes a fluid which expands at body temperature.

22. The device of claim 18, wherein said working fluid chamber includes an outlet through which said working fluid exists via a connecting means connected to said valve to pressurize said stiffener means when said valve is opened.

23. The device of claim 18, wherein said root portion is implanted in the root of the corpous cavernosum, and said pendulous portion is implanted in the pendulous portion of the penis.

24. A penile erection device that is fully implantable in a patient, said device comprising:
   stiffener means adapted for implantation in the penis, said stiffener mdans including a root portion and a pendulous portion;
   a fluid reservoir containing a pressurized fluid in flow communication with said stiffener means; and
   valve means located intermediate said root portion and said pendulous portion for controlling flow between said fluid reservoir and said stiffener means, said valve means being closed to maintain the penis in one of an erect state and a flaccid state and being open to allow the penis to change to one of the flaccid state and the erect state, and said valve means being adapted to be located in the corpous cavernosum of the penis so as to be opened in response to manual movement of the penis laterally out of one of a flaccid state position and an erect state position of the penis, and closed upon movement of the penis to one of the erect state and the flaccid state positions.

25. The device of claim 24, wherein a connecting means interconnects said fluid reservoir and said stiffener means.

26. The device of claim 24, wherein said valve means is movable between a first position assumed when said stiffener means is in a first position, and a second position assumed when said stiffener means is in a second position, said valve means being closed in its first position to maintain the penis in one of said erect state and said flaccid state and being open in its second position to allow the penis to change to one of said flaccid state and said erect state.

27. The device of claim 24, wherein said valve means is movable to the open and closed positions in response to lateral movement of the penis upward against the patient's abdomen.

28. The device of claim 24, wherein said valve means comprises lever means for moving said valve means between the closed first position and open second position, said lever means extending into a pendulous portion of said stiffener means for movement in response to said manual lateral movement of the penis.

29. The device of claim 28, wherein said valve means comprises a fixed base member and a movable ball member, and said lever means is mounted at one end on said ball member.

30. The device of claim 29 wherein said ball member is retained on said fixed member by one end of a guide member of split construction at an opposite end to facilitate mounting of said guide member on said base member.

31. The device of claim 29, wherein said ball member and said lever means includes respective fluid passageways in communication with one another, with the fluid passageway in said lever means opening into a fluid chamber in said pendulous portion of said stiffener means.

32. The device of claim 29, wherein:
   said lever means comprises spherical means on an opposite free end of said lever means;
   said ball member is retained on said fixed member by one end of a guide member of split construction at an opposite end to facilitate mounting of said guide member on said base member; and
   said ball member and said lever means include respective fluid passageways in communication with one another, with the fluid passageway in said lever means opening into a fluid chamber in said pendulous portion of said stiffener means.

33. The device according to claim 28 wherein said lever means comprises spherical means on a free end of said lever means.

34. A penile erection device that is fully implantable in a patient, said device comprising:
   stiffener means adapted for implantation in the penis, said stiffener means including a root portion which is implanted in the corpus cavernosum of the penis, a pendulous portion which is implanted in the pendulous portion of the penis, and a valve,
   said valve being open and allowing fluid to pass into said pendulous portion when the pendulous portion is in a predetermined position with respect to said root portion;

a fluid reservoir being in flow communication with said pendulous portion when said valve is open;

a working fluid located in said fluid reservoir to flow from said fluid reservoir into said pendulous portion when said valve is open; and said fluid reservoir including a sealed, variable volume pressurant chamber, a fluid reservoir chamber whose volume is dependent upon the volume of said variable volume pressurant chamber, a pressurant filling said pressurant chamber and said working fluid filling said fluid reservoir chamber, said pressurant being capable of changing state at normal body temperature in dependence upon the volume of said pressurant chamber to force said working fluid from said fluid reservoir chamber.

35. The device of claim 34, wherein a pendulous chamber is located in said pendulous portion, said pendulous chamber being in flow communication with said fluid reservoir chamber via said valve, said valve allowing the penis to change from the flaccid state to the erect state when the volume of said pressurant chamber is increased to deliver said working fluid from said fluid reservoir chamber to said pendulous chamber.

36. The device of claim 35, wherein said valve is a manually operated valve intermediate said fluid reservoir chamber and said pendulous chamber so that when said valve is opened, the pressurant in said pressurant chamber is permitted to expand and thereby increase the volume of said pressurant chamber.

* * * * *

UNITED STATES PATENT AND TRADEMARK OFFICE
CERTIFICATE OF CORRECTION

PATENT NO. : 4,671,261
DATED : June 9, 1987
INVENTOR(S) : Robert E. Fischell

It is certified that error appears in the above-identified patent and that said Letters Patent is hereby corrected as shown below:

Claim 16, column 7, line 4, "12" should read --13--.

Claim 16, column 7, line 5, "end" should be inserted between "one" and "of".

Claim 17, column 7, line 8, "12" should read --13--.

Claim 19, column 7, line 34, "11" should read --18--.

Signed and Sealed this

Ninth Day of May, 1989

Attest:

DONALD J. QUIGG

Attesting Officer

Commissioner of Patents and Trademarks